(12) United States Patent
Kamp

(10) Patent No.: US 7,008,407 B1
(45) Date of Patent: Mar. 7, 2006

(54) URINE COLLECTION METHOD AND APPARATUS

(75) Inventor: David C. Kamp, Grand Rapids, OH (US)

(73) Assignee: Owens-Illinois Closure Inc., Toledo, OH (US)

( * ) Notice: Subject to any disclaimer, the term of this patent is extended or adjusted under 35 U.S.C. 154(b) by 297 days.

(21) Appl. No.: 10/252,918

(22) Filed: Sep. 23, 2002

(51) Int. Cl.
*A61M 1/00* (2006.01)

(52) U.S. Cl. ....................................... 604/327; 604/327
(58) Field of Classification Search ................ 604/317, 604/323, 327
See application file for complete search history.

(56) References Cited

U.S. PATENT DOCUMENTS

| | | | |
|---|---|---|---|
| 3,374,939 A | | 3/1968 | McMenimen |
| 3,529,599 A | | 9/1970 | Van Nuys et al. |
| 3,598,150 A | * | 8/1971 | Nolan .................... 137/625.32 |
| 3,651,810 A | | 3/1972 | Ormerod |
| 4,280,498 A | * | 7/1981 | Jensen ........................ 604/335 |
| 4,421,509 A | | 12/1983 | Schneider et al. |
| 4,462,510 A | * | 7/1984 | Steer et al. .................... 222/48 |
| 4,634,437 A | | 1/1987 | Lowthian |
| 4,661,100 A | | 4/1987 | Rechsteiner |
| 4,828,554 A | | 5/1989 | Griffin |
| 5,496,300 A | | 3/1996 | Hirsch et al. |
| 5,616,138 A | | 4/1997 | Propp |
| 6,045,542 A | | 4/2000 | Cawood |
| 6,132,407 A | | 10/2000 | Genese et al. |

* cited by examiner

*Primary Examiner*—Tatyana Zalukaeva
*Assistant Examiner*—Ginger Chapman

(57) ABSTRACT

A urine collection device (10) that is made up of a flexible, thermoplastic urine collection bag (20), which receives urine through a molded plastic inlet fitment (30) that is secured to an upper end of the bag 5 and discharges urine through a two-piece molded plastic valve fitment (40) at a lower end of the bag. The inlet fitment, which has no check valve therein, has a series of steps gradually reducing lateral extent as it extends longitudinally from the bag to a free end thereof, and each of the steps extends at a non-perpendicular angle to the longitudinal central axis of the inlet fitment. The bag is also free of any check or flutter valve. The outlet valve fitment has a fixed outer element (42) surrounding an inner element (44) that is rotatable with respect to the outer element to selectively open or close the outlet valve fitment to flow.

6 Claims, 3 Drawing Sheets

URINE COLLECTION METHOD AND APPARATUS

FIELD OF THE INVENTION

This invention relates to a method of and an apparatus for collecting urine from a human patient. More particularly, this invention relates to a method and apparatus of the foregoing character that reduces the number of parts required in collecting urine according to known urine collection methods and apparatus.

BACKGROUND OF THE INVENTION

U.S. Pat. No. 4,828,554 (Griffin) discloses a urine collection device that includes a collection bag (12) into which urine flows through a line that has a one way flow valve (10) in it, the bag and valve being separate elements. The requirement that the valve and the bag be separate elements involves costs in manufacturing and assembly of the elements that could be reduced if the functions of these elements could be combined into a single element.

Other known prior art urine collection devices, for example, as taught by U.S. Pat. No. 4,421,509 (Schneider et al.), substitute a separate member in the urine collection bag, which is usually called a flutter valve, to serve the function of the one-way valve of the aforesaid '554 patent, namely, to prevent urine from flowing or splashing in reverse from the bag back through the inlet fitment into an inlet tube that is normally connected to the fitment. The requirement for the incorporation of such a flutter valve also requires an element separate from the bag itself, and the manufacturing and assembly costs of such a device could also be reduced by combining the function of the bag and a separate one-way valve within the bag.

Another feature of known urine collection devices, for example, as taught by the aforesaid '509 patent, is the incorporation in the inlet fitment of the device of a plurality of steps of gradually reduced extent approaching the free end of the fitment in order to permit inlet tubes of varying internal diameters to be attached to the fitment. However, the varying extents of such steps, which extend normally of a flow axis of the fitment, can often lead to difficulty in manually, securely attaching an inlet tube to the inlet fitment.

It is also known that a normally-closed outlet fitment be attached to a bag of a urine collection device at an end opposed to the end to which the inlet fitment is attached. The aforesaid '509 patent teaches this construction. Such an outlet fitment usually incorporates an operable but normally-closed valve or clamp for manipulation by a user to empty the bag when the bag is strapped to a leg of the user. While U.S. Pat. No. 4,634,437 (Lowthian) discloses an outlet valve (slide tab 9) for a urine collection device that assertedly has one-hand opening characteristics (column 2, lines 47–51), most known prior art urine collection devices have outlet fitments with valves that require the patient to whom the device is secured to use both hands in opening and closing the valve.

As is taught, for example, in U.S. Pat. No. 5,496,300 (Hirsch et al.), it is also important for many urine collection devices that they be capable of being removably strapped to a leg of user, both at a location near an inlet to the collection bag of the device and at a location near an outlet from the collection bag. However, the device of the '300 patent requires the use of a pair of straps at each location, with a releasable hook and loop (Velcro) connection between free ends of each, and this is an expensive construction. It is known that a single elastic strap can be substituted for the dual strap of the aforesaid '300 patent with a button at each inlet and outlet fitment around which the elastic strap at that location can be looped. However, known elastic strap engaging devices involve the use of a separate, molded strap-receiving button at each location, and this involves additional manufacturing and assembly costs that could be avoided if the strap receiving button at each location was molded integrally in a single piece with the fitment with which it is associated.

SUMMARY OF THE INVENTION

According to the present invention there is provided a urine collection method and apparatus in which urine is collected in a flexible bag that does not require a separate flutter or one-way valve, either within the bag itself or in an inlet fitment that is secured to the bag, to prevent reverse flow or splashing from the bag into the fitment, or even into an inlet line secured to the fitment. The bag of the urine collection device of the present invention has a heat-staked line extending partly across the bag, at a location near the inlet to the bag and in alignment with the inlet, the free-end (s) of the heat-stake line forming an internal funnel within the bag beyond the free end(s) of the line to allow urine to flow to a lower part of the bag. As the bag fills, its expanding shape closes the funnel, to thereby prevent any reverse flow or splashing of urine from the part of the bag below the heat-stake line to the part there above, and achieving such result without the need for a separate flutter valve or other one-way valve.

The urine collection device according to the preferred embodiment of the present invention also has a one piece inlet fitment heat-staked at the location of an opening at an otherwise closed end of a flexible thermoplastic collection bag. The fitment has the external configuration of a series of steps of reducing extent approaching the free end of the fitment to facilitate attachment of inlet tubes of varying I.D. to the fitment. The steps of the inlet fitment of the present invention extend non-perpendicularly to a longitudinal central axis of the fitment to reduce the force required to insert a tube over the step whose outside diameter is slightly larger than the inside diameter of the tube. The inlet fitment also has an integrally-closed free end that is easily removable at the time of first use to attain maintenance of cleanliness conditions within the urine collection device until it is ready for use, and, to achieve this result without the need for a separate closing member.

The urine collection device of the present invention also has a two-piece outlet fitment, an outer, fixed member of which is heat-staked to the urine collection bag at the location of an opening of an otherwise closed outlet or lower end of the bag of the urine collection device. The outlet fitment also has an inner valve member that is movable within and with respect to the fixed outer valve member between open to flow and closed to flow positions, and the movement of the inner valve member is manually by a patient to whom the bag is removably attached, and may be done in a single-hand motion. Fluid moves within the outlet fitment inner valve member, which is annular in cross-section with a closed, innermost free end in a straight through manner, with the seat between an innermost, frusto-conical surface on the inner valve member and a complimentary frusto-conical seat on the outer valve member. Slots in a well of the inner valve member, near its closed end, permit fluid to be withdrawn from the bag of the urine collection device to flow through the interior of the inner valve, the valve also having an annular seal at a location between its closed end and its outer end to prevent fluid from escaping in an annulus between the inner valve member and the outer valve member.

Each of the inlet fitment and the outlet fitment is preferably provided with an integral button with an enlarged free end about which an elastic band can be looped to permit rapid attachment and disattachment of the urine collection device of the present invention to a leg of a user. In the case of the inlet fitment, the integral button is a part of the one-piece construction of the inlet fitment. In the case of the outlet fitment, the integral button is the part of the outer valve member of the outlet fitment.

Accordingly, it is an object of the present invention to provide an improved method of and apparatus for collecting urine from a patient. More particularly, it is the object of the present invention to provide a method and apparatus of the foregoing character that is simpler in construction, while still being functionally in compliance with all known requirements, than known prior art urine collection devices and methods.

For a further understanding of the present invention and the objects thereof, attention is directed to the drawing in the following brief description thereof, to the detailed description of the invention and to the appended claims.

IN THE DRAWINGS

DETAILED DESCRIPTION OF THE INVENTION

Figure 1:
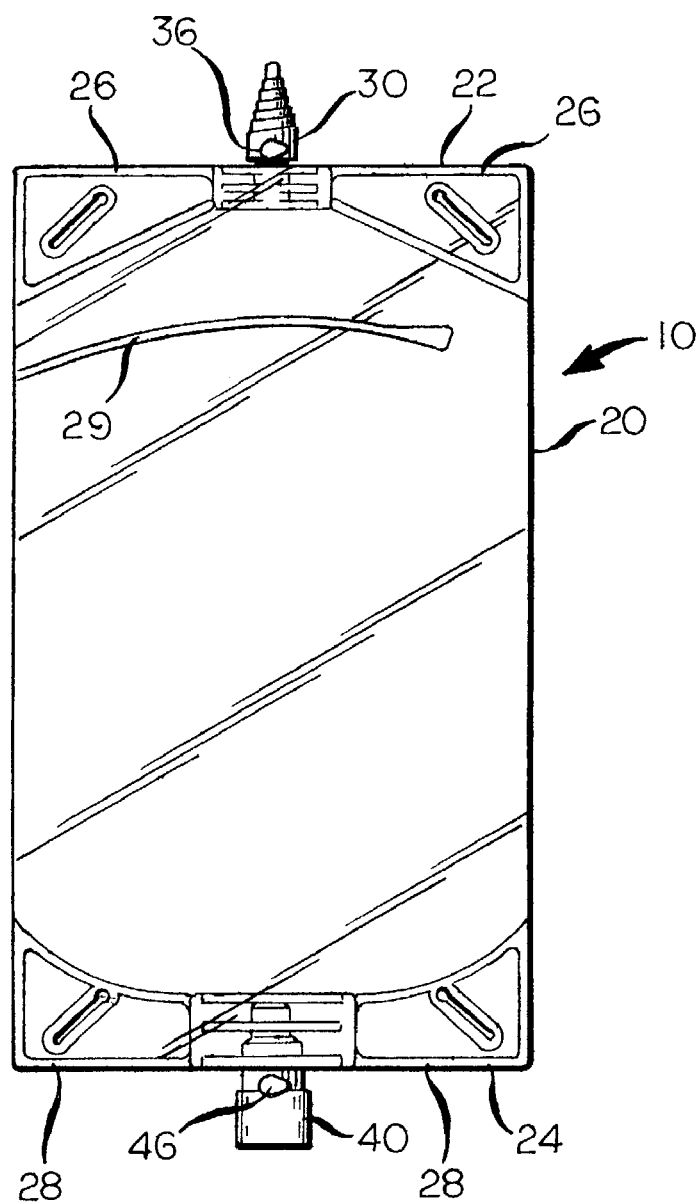
FIG. 1 is an elevation view of a urine collection device according to the preferred embodiment of the present invention.
Figure 2:
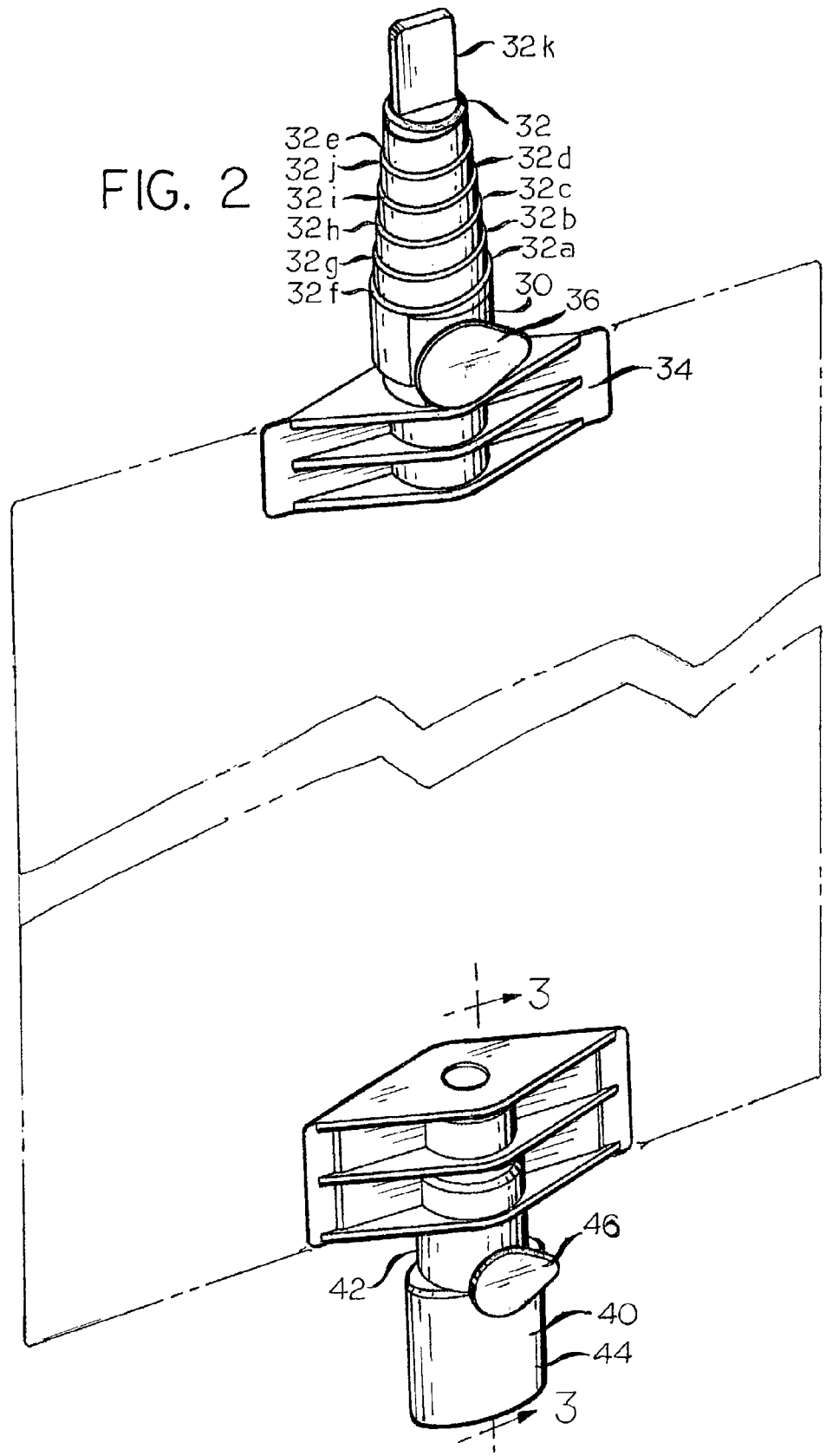
FIG. 2 is a perspective view, at an enlarged scale showing certain of the elements of FIG. 1 in their assembled state.
Figure 4:
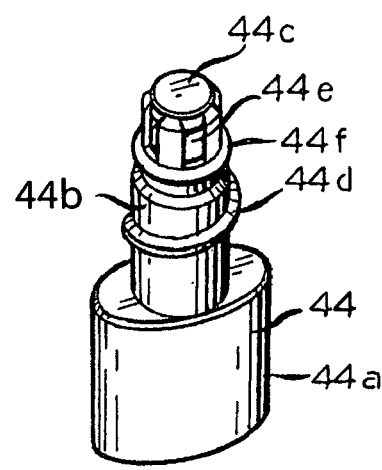
FIG. 4 is a perspective view at a reduced scale of an element of the structure illustrated in FIG. 3.

A urine collection device according to the present invention is generally indicated in FIG. 1 by reference numeral 10. The urine collection device 10 is made up of a flexible, urine collection bag 20, an inlet fitment 30 by which urine can be introduced into the flexible bag 20 and an outlet fitment 40, which functions as a valve and by which urine contained in the bag 20 may be withdrawn therefrom, when desired.

The urine collection bag 20 is fabricated from a flexible sleeve of a suitable plastic material, for example, polyethylene or polyvinyl chloride. The bag 20 is initially open at its upper and lower ends 22, 24, respectively, and the inlet fitment 30, which is molded in one piece from a thermoplastic material that is capable of being heat-staked to the bag 20, is heat-staked to an opening at the upper end 22 of the bag 20, the upper end 22 otherwise being closed to flow by heat-staking along lines identified by reference numerals 26. Likewise, the outlet fitment 40, which is molded in two pieces 42, 44, as will be hereinafter described more fully, has an outer piece 42, which is molded from a thermoplastic material that is capable of being heat-staked to the bag 20. The outer piece 42 is heat-staked to an opening at the lower end 24 of the bag 20, the lower end 24 otherwise being closed to flow by heat-staking along lines identified by reference numeral 28. The bag 20 is also heat-staked along a line 29 that is positioned closer to the inlet fitment 30 than to the outlet fitment 40 and extends from a side edge of the bag 20 partly to an opposed side edge, as will be hereinafter described more fully.

The inlet fitment 30, which is generally in the shape of an inverted T, has a shank portion 32, which extends away from the bag 20, and a head portion 34, which is the portion that is directly heat-staked to the bag 20. The shank portion 32 has a series of steps 32a–32e of decreasing lateral extent as the shank portion 32 extends away from the bag 20, the steps 32a–32e being separated from one another by a series of annular shoulders 32f–32j, respectively. This construction facilitates attachment of a free end of a flexible tube (not shown) from a catheter or the like to be attached to the shank portion 32 of the inlet fitment, at least one of the various steps 32a –32e being slightly greater in outside diameter than an inside diameter of the flexible tube, to permit the tube to be quickly, frictionally attached to the inlet fitment 30. In that regard, each of the shoulders 32f–32j extends obliquely to a longitudinal central axis of the inlet fitment 30 so that an interior of an inlet tube can be gradually inserted thereover.

The inlet fitment 30 also has a button 36 integrally molded with the inlet fitment 30 at a location on the shank portion 32 that is near the head portion 34. The purpose of the button 36 is to permit an elastic band (not shown) to be removably secured to the inlet fitment 30 to permit the urine collection device 10 to be removably secured to a leg of a patient user. Further, the shank portion 32 of the inlet fitment 30 has an integrally closed free end 32k that can be quickly removed by severing, from the rest of the structure of the shank portion 32, which is annular in configuration. The free end 32k of the shank portion 32 serves to maintain cleanliness within the urine collection device 10 until it is ready for use, and it performs this function without the need for a separate closing member.

Figure 3:
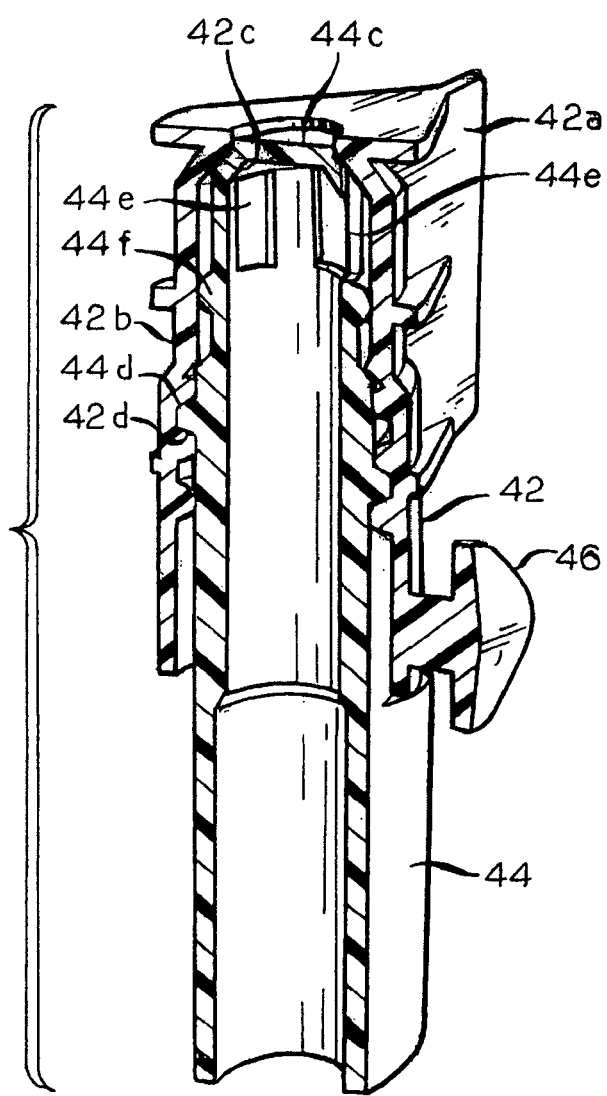
FIG. 3 is a sectional view taken on line 3—3 of FIG. 2.

The outer piece 42 of the outlet fitment 40 is generally T shaped, with the head portion 42a, which is heat-staked to the lower end 24 of the bag 20, and an annular shank portion 42b. The inner piece 44 is received in an annulus of the shank portion 42b of the outer piece 42 and serves to permit or prevent urine from flowing from the bag 20 through the outlet fitment 40, a free, end 44a of the inner piece 44 being of oval or other non-circular configuration to permit the inner piece 44 to be manually turned within the shank portion 42b of the outer piece 42. The inner piece 44 has an inner portion that is annular in configuration except for a closed, innermost end 44c that is frusto-conical in cross-section end seats against a frusto-conical seat 42c of the outer piece 42 in the closed to flow position of the inner piece 44, which is the position shown in FIG. 3. The inner end portion 44b of the inner piece 44 has an outer helical thread 44d that engages in a helical thread 42d of the outer piece 42, so that turning of the inner piece 44 will break a seal between the innermost end 44c of the inner piece 44 and the outer piece 42. This will allow urine to flow from the bag 20 into the inner piece 44 by way of slots 44e in the inner piece 44 near the inner most end 44c of the inner piece 44. An outwardly projecting bead 44f on the inner piece 44, at a location in alignment with the bottoms of the slots 44e, sealingly engages an inside diameter of the shank portion 42b of the outer piece 44 to confine the escape of urine to the interior of the inner piece 44. The outer piece 42 of the outlet fitment 40 also has a button 46 molded integrally therewith at a location on the outer piece 42 that is near the lower end 24 of the bag 20 to permit a second elastic band (also not shown) to be removably secured to the outlet fitment 40, to further permit the urine collection device 10 to be removably secured to a leg of a patient user.

Although the best mode contemplated by the inventor for carrying out the present invention as of the filing date hereof has been shown and described herein, it will be apparent to those skilled in the art that suitable modifications, variations, and equivalents maybe made without departing from the scope of the invention, such scope being limited solely by the terms of the following claims and the legal equivalents thereof.

I claim:

1. A urine collection device comprising:
   a bag, said bag being fabricated from opposed layers of a thermoplastic material and being closed around its periphery but for an inlet opening at an end and an outlet opening at an opposed end;
   an inlet fitment sealingly joined to said bag at said inlet end;
   and an outlet fitment having an outer element sealingly joined to said bag at said outlet opening, said outlet fitment further having an inner element within said outer element;
   said outer element including an annular shank portion extending along an axis and having an inner thread and frusto-conical seat; and
   said inner element including (i) a closed innermost end with a frusto-conical portion sealingly engageable with said frusto-conical seat and (ii) an outer thread engaged to said inner thread, rotation of said inner element relative to said outer element moving said inner element axially relative to said outer element to move said frusto-conical portion into sealing engagement with said frusto-conical seat and out of sealing engagement.

2. A urine collection device according to claim 1 wherein:
   said inner element has a plurality of slots in said annular wall at a location adjacent to said closed end.

3. A urine collection device according to claim 2 wherein:
   said inner element has an external bead at a location aligned with bottoms of said plurality of slots, said external bead sealingly engaging an inside of a wall of said outer element to confine flow through said outlet fitment to an interior of said inner element.

4. A urine collection device according to claim 1 wherein:
   said outer element of said outlet fitment has a button molded integrally therewith for removably receiving an elastic strap to permit said urine collection device to be removably secured to a leg of a patient user.

5. A urine collection device according to claim 1 wherein:
   said inlet fitment has a button molded integrally therewith for removably receiving an elastic strap to permit said urine collection device to be removably secured to a leg of a patient user.

6. An outlet valve fitment according to claim 1 wherein:
   said inner element has an external bead at a location in alignment with said plurality of slots, said bead slidingly and sealingly engaging the annular wall of said outer element to confine flow of fluid from the article through said outlet valve fitment to the interior of said inner element.

* * * * *